(12) United States Patent
De Oliveira et al.

(10) Patent No.: US 8,439,758 B2
(45) Date of Patent: May 14, 2013

(54) MEDICATION COMPLIANCE USING PERSUASIVE COMPUTING

(75) Inventors: Rodrigo De Oliveira, Madrid (ES); Mauro Cherubini, Madrid (ES); Nuria Oliver, Madrid (ES)

(73) Assignee: Telefonica, S.A., Madrid (ES)

( * ) Notice: Subject to any disclaimer, the term of this patent is extended or adjusted under 35 U.S.C. 154(b) by 115 days.

(21) Appl. No.: 13/026,648

(22) Filed: Feb. 14, 2011

(65) Prior Publication Data
US 2011/0201421 A1    Aug. 18, 2011

Related U.S. Application Data

(60) Provisional application No. 61/304,691, filed on Feb. 15, 2010.

(51) Int. Cl.
*A63F 9/24* (2006.01)

(52) U.S. Cl.
USPC ........................................ 463/42; 39/40; 39/41

(58) Field of Classification Search ............... 463/39–42
See application file for complete search history.

(56) References Cited

U.S. PATENT DOCUMENTS
2006/0234793 A1* 10/2006 Walker et al. ................... 463/20

OTHER PUBLICATIONS

Russell, Cynthia L., et al., "Older Adult Medication Compliance: Integrated Review of Randomized Controlled Trials" *Am J. Health Behav.*, 2006;30(6):636-650.
"Focused R&D guarantees timely innovation to meet future demands",*AARDEX group*, Jul. 14, 2010.

* cited by examiner

*Primary Examiner* — Omkar Deodhar
(74) *Attorney, Agent, or Firm* — Ladas & Parry LLP

(57) ABSTRACT

The invention refers to a method for encouraging a user to comply with his/her medication regimen, comprising the steps of:
  registering a group of parameters related to a medication intake of said user, which parameters include a time parameter and a user identifier;
  sending said group of parameters related to a medication intake of the user to a server (40);
  computing a time difference between said time parameter received and a time parameter associated to said user identifier previously recorded in the server;
  assigning said user with a pre-established number of points depending on the value of said time difference; and
  providing said user with information regarding his/her points obtained for the medication intake, including a summary of their medication compliance status using appealing personal awareness.
  providing symbolic rewards (e.g., listening to a favorite song, being surprised with a family photo, reading a joke) to said user if he/she complies with his/her medication regimen
  providing means to said user to contact/remind other users in case they forget to take their medication.

3 Claims, 3 Drawing Sheets

MEDICATION COMPLIANCE USING PERSUASIVE COMPUTING

This application claims the benefit of U.S. Provisional Application(s) No(s): Application No. 61/304,691 filed Feb. 15, 2010.

FIELD OF THE INVENTION

The present invention relates generally to systems that help patients comply with their medication obligations by means of persuasive computing.

BACKGROUND OF THE INVENTION

Medication compliance is a critical component in the success of any medical treatment. However, a recent review of 139 studies reporting compliance data showed that only 63% of patients continue with their medication after a year and patients take their medication only 72% of the time. The World Health Organization envisions a more pessimistic scenario estimating that only 50% of patients follow their doctors' prescriptions. The scenario is even more worrying for the elderly, where the levels of noncompliance may reach 75%.

In order to tackle this challenge, medical experts have tried a variety of strategies that remind patients to take their medication, including: (1) counseling, (2) simplified regimen plans, and (3) compliance aids.

The counseling strategy focuses on patient education, including risk factors of non-compliance, information about their illness, instructions on how to take the prescribed medication correctly, and explanations of the benefits and possible adverse effects of the therapy. This method has been extensively applied yielding mixed results in different studies. For instance, Russell et al. identified that 21 out of 42 studies on counseling interventions did not reveal any difference between treatment and control groups, while the remaining 21 studies did (Russell, C. L.; Conn, V. S.; Jantarakupt, P. "*Older adult medication compliance: integrated review of randomized controlled trials*". American Journal of Health Behavior 30, 2006).

Simplified regimen plans include drug reminder charts, calendar packaging, and dosage boxes. These studies reveal that this strategy alone is unlikely to improve drug compliance.

Finally, compliance aid has proven to be one of the most effective strategies to date. For instance, telephone follow-ups by the pharmacist were extensively tested and proven to be effective in enhancing medication compliance while also reducing the overall cost to the health provider. However, this intervention method does not scale well for a large population on a long-term basis. Many simpler reminders are available on the market, such as the e-Pill Multi-alarm Pocket, the 6-alarm vibrating watch, and the GlowCaps pillbox which also record date and time every time it is opened (similar to MEMS). Still, previous work reports cases in which no improvement in medication compliance was observed by using reminders alone, or even where automated reminders were perceived negatively by the users.

Combinations of these strategies have been frequently proposed in the literature with the assumption that a single approach cannot be effective for all patients. An example is the use of both counseling strategies and compliance aids to trigger the patients' motivation towards adherence to medication. However, this approach has been shown to be ineffective in a few cases according to both objective and subjective measures.

The main problem in current medication compliance strategies is that they mainly focus on reminding patients of something they already know they have to do, without engaging them in doing it by themselves.

In fact, the mobile and pervasive technologies that have been proposed to tackle this challenge are mainly in the form of memory aid solutions that remind patients to take their pills. However, these methods do not engage patients in shifting their behavior towards better compliance. In fact, alerting patients to do the same thing every day does not engage them in actually doing it themselves.

SUMMARY OF THE INVENTION

The present invention refers to a method and system for encouraging a user to comply with his/her medication regimen according to claims 1 and 8, respectively. Preferred embodiments of the method are defined in the dependent claims.

The present invention aims at increasing levels of compliance (remembering to take a dose) and adherence to medication regimens (taking doses at the prescribed time) by focusing on changing the way people perceive the drug intake task. Specifically, the present solution focuses on the fact that patients become more compliant in taking their medications when the task is not seen as an obligation, but rather as an engaging experience.

In order to provide such an engagement, the present invention proposes a method and a system with four components: social competition, social support, appealing personal awareness and virtual reward.

In a first aspect of the invention, the method for encouraging a user to comply with his/her medication regimen entails the following steps:

registering a group of parameters related to a medication intake of said user, which parameters include a time parameter and a user identifier;

sending said group of parameters related to the user's medication intake to a server;

computing a time difference between said time parameter received and a time parameter associated to said user identifier previously recorded in the server;

assigning said user with a pre-established number of points depending on the value of said time difference; and providing said user with information regarding his/her points obtained for the medication intake.

Preferably said registration of a group of parameters related to a medication intake of the user is carried out by directly entering said group of parameters in a computing device.

Said registration of a group of parameters related to a medication intake of the user can also be carried out by means of a pillbox equipped with a sensor configured to record said parameters upon detecting opening of a pillbox lid.

The step of sending said group of parameters related to a medication intake of the user to a server preferably comprises:

sending said group of parameters related to a medication intake of the user from the pillbox to a computing device, the pillbox being further provided with a short-range communication interface to said computing device, and the computing device having:

a short-range communication interface for receiving said group of parameters from the pillbox, and a communication interface to a data network to which the server is connected for sending said group of parameters related to a medication intake of the user.

The step of sending said group of parameters related to a medication intake of the user can also comprise:

sending directly said parameters from the pillbox to the server, the pillbox being further provided with a communication interface to a data network to which the remote server is connected.

In a preferred embodiment, the number of points assigned to the user is a first number of points if the value of said time difference is lower than a first pre-established threshold, and said number of points assigned to the user is a second number of points if the value of said time difference is greater than said first threshold, said first number of points being bigger than said second number of points.

Said number of points assigned to the user can be set to zero if the time difference is greater than a pre-established second threshold.

A second aspect of the invention refers to a system for encouraging a user to comply with his/her medication regimen, comprising a plurality of users making use of the method defined hereinbefore, wherein each user is provided with means for accessing to information regarding the other user's points.

Preferably, an alert is sent to a first user whenever the time difference computed by the server for a second user is greater than a pre-established second threshold.

BRIEF DESCRIPTION OF THE DRAWINGS

To complete the description and in order to provide a better understanding of the invention, a set of drawings is provided. Said drawings form an integral part of the description and illustrate preferred embodiments of the invention, which should not be interpreted as restricting the scope of the invention, but just as examples of how the invention can be embodied. The drawings comprise the following figures.

DETAILED DESCRIPTION OF THE PREFERRED EMBODIMENTS

Figure 1:
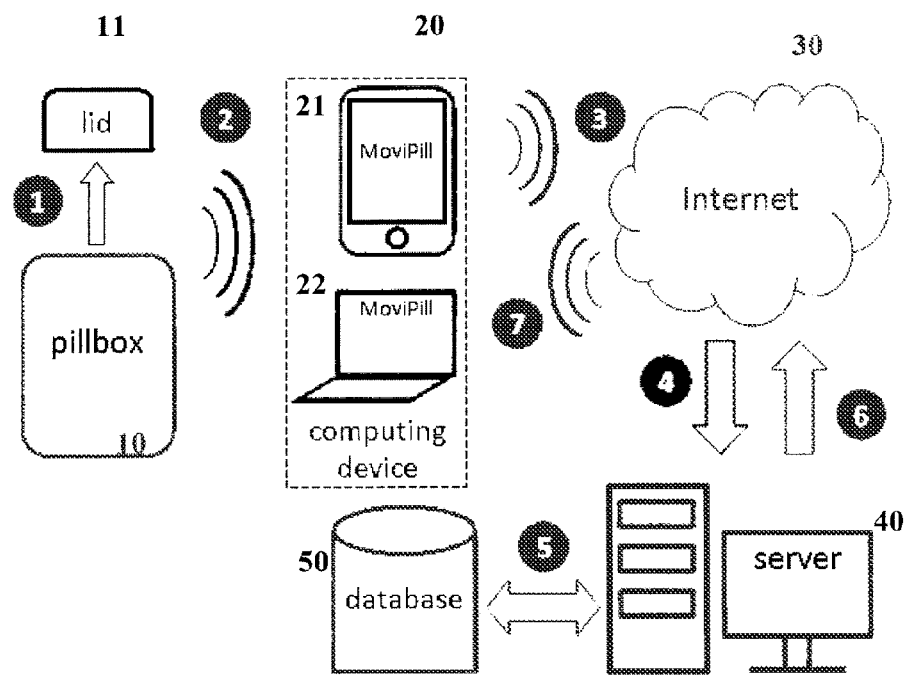
FIG. 1 illustrates the system's architecture according to an embodiment of the present invention.

Reference will now be made in detail to a preferred embodiment of the present invention, whose system architecture can be explained by the following scenario, sketched in FIG. 1:

Consider a user that takes two doses per day of a certain medication. For the first dose of the day, the user opens the pillbox 10 containing the medication and takes a dose of it. On the inner part of the pillbox lid 11, there is a sensor that registers date and time the pillbox was opened (step 1), in a way similar to current technology, e.g. MEMS by Aardex (available at: http://www.aardexgroup.com/aardex_index-.php?group=aardex&id=85, accessed on January 2011). The data is sent wirelessly (step 2) to a nearby computing device 20 that runs the proposed system (e.g., mobile phone 21, PC 22, etc.). Whenever the computing device 20 is connected (step 3) to the Internet 30, it sends (step 4) to a server 40 the identifiers of both the user and the medication, and the date and time that the pillbox was opened (medicine supposedly taken). On the server side, the user's information is validated and his/her medication intake profile is updated in a database 50 (step 5). Finally, the server 40 sends a confirmation back to the computing device via the Internet, which updates the status of the game (step 6 and step 7).

An alternative implementation to the previous scenario (not shown) enables the pillbox 10 to send the information directly to the server 40 without the need for the pillbox to be closer to a computing device running the proposed system at the moment of the drug intake. This approach entails extra complexity to the pillbox manufacturing.

The proposed invention was evaluated by conducting a field study in which the competition component 301 (FIG. 3) was tested. Eighteen elders (50-75 years old) were recruited from the database of a social foundation service. Each user was assigned the mobile phone 21, a HTC smartphone (model P3300), with its charger. Each user was also provided with the pillbox 10 equipped with a sensor (maker AARDEX model MEMS 6).

The smartphone is able to transmit data over the GSM cellular network. Medication intake information is entered by the user via a mobile application (named "MoviPill"), which runs on the mobile device; said information is transmitted in real time to the remote server 40.

Whenever the Internet 30 connection is lost, the application keeps a local log of the medication intake and attempts to re-establish the connection after every 10 seconds. When one of these attempts is successful, the previously saved medication intake data is sent to the server 40. In addition, the MoviPill application refreshes the status after every 5 minutes to ensure the data presented is updated.

The pillbox records the intake information independently from the mobile phone and these logs are used as an independent measure of medication compliance as explained below.

The present proposal focuses on the fact that patients become more compliant in taking their medications when the task is not seen as an obligation, but rather as an engaging experience. In order to provide such engagement, the present solution implements four components:

Social competition: the MoviPill application is a sort of a game in which the "winner" is the user who takes his/her medication as prescribed by the doctor (both in terms of compliance and adherence to the regimen). All users of the application participate in the game and are part of a social network.

Social support: "Players", i.e. patients, are able to chat with each other using the communication tools available to the application's social network and also get extra points whenever they remind other players to take their doses (in case they are delayed).* Appealing at-a-glance personal awareness: Players can check their medication compliance status simply by looking at the appearance of an engaging computer graphics character that is shown in the idle screen of their mobile phone (e.g., if the character is a dog, it looks happy in case the patient is being compliant and sick otherwise);

Virtual reward: Players are surprised with a family photo, a favorite song, or a poem/joke every time they take their medication on time.

In order to simplify the proposed solution, users have only one goal: to take their medication as close as possible to the time prescribed by their doctor. The closer to the prescription time, the more points the patient obtains; for example:

(a) two points if the intake occurs within ±15 min of the prescribed time;

(b) one point if the patient takes his/her medication within ±15 to ±30 min of the prescribed time;

(c) zero points if within ±30 min to ±hours; and (d) −1 point if the patient forgets to take his/her medication.

Figure 2:
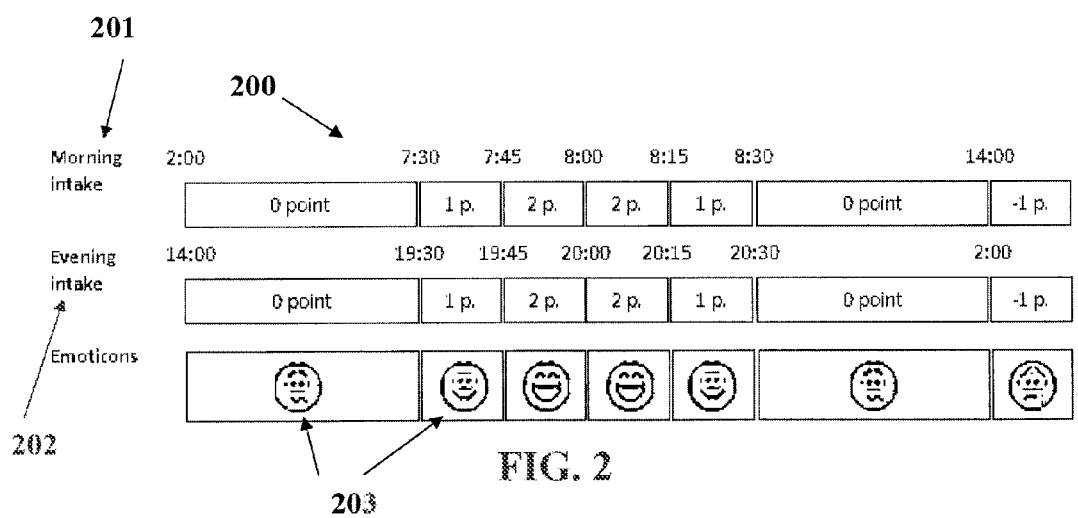
FIG. 2 shows a screenshot of an example of points and emoticon assignments for a patient that takes two doses per day of a certain medication.

FIG. 2 shows a possible screenshot 200 of the game dynamics for a patient that takes two doses per day, a morning intake 201 at 8 am and an evening intake 202 at 8 pm. It also shows the emoticons 203 assigned in each case.

In an implementation of the invention, the smartphone interface is designed considering that elders might be the most interested customers. Therefore, special care is devoted to the system's layout and interaction. Buttons and dialogs are personalized with bigger fonts and higher color contrast, while touchscreen interaction is preferably enabled without the need of using a pen stylus.

Figure 3:
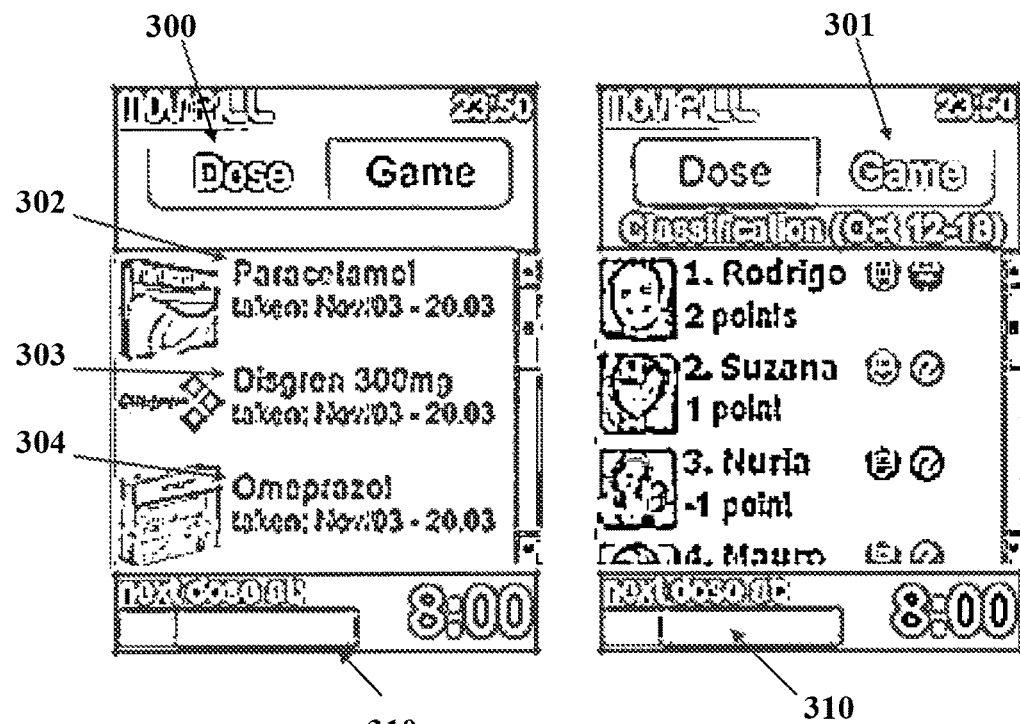
FIG. 3 shows an implementation of the game interface for a smartphone, showing the dose screen on the left and the game screen on the right.

One possible implementation is presented in FIG. 3:

The Dose screen 300 presents information about the date and time that each medication is taken (pillbox opened) together with the time of the next intake and a progress bar 310 informing how much time is left to the next dose. The interface in the example monitors intakes of several medications, i.e., Paracetamol 302, Disgren 300 mg 303, Omeprazol 304.

The Game screen 301 displays the status of the medication compliance game, showing the ranking of users by the end of the first day of competition. Special attention is dedicated to including social competition without violating the players' privacy. Hence, the data on this screen, which is shared with the other players, does not provide any information on the medication that each player was taking. Emoticons are used to represent how compliant participants are on each dose (see also bottom part of FIG. 2), without revealing the exact time of taking their medication. The number of emoticons next to each participant's score corresponds to the number of doses prescribed per day and the emoticon represents how compliant they were with that dose. A social network is created with all the participants and social competition is implemented by ranking all players according to their score in the compliance game.

Figure 4:
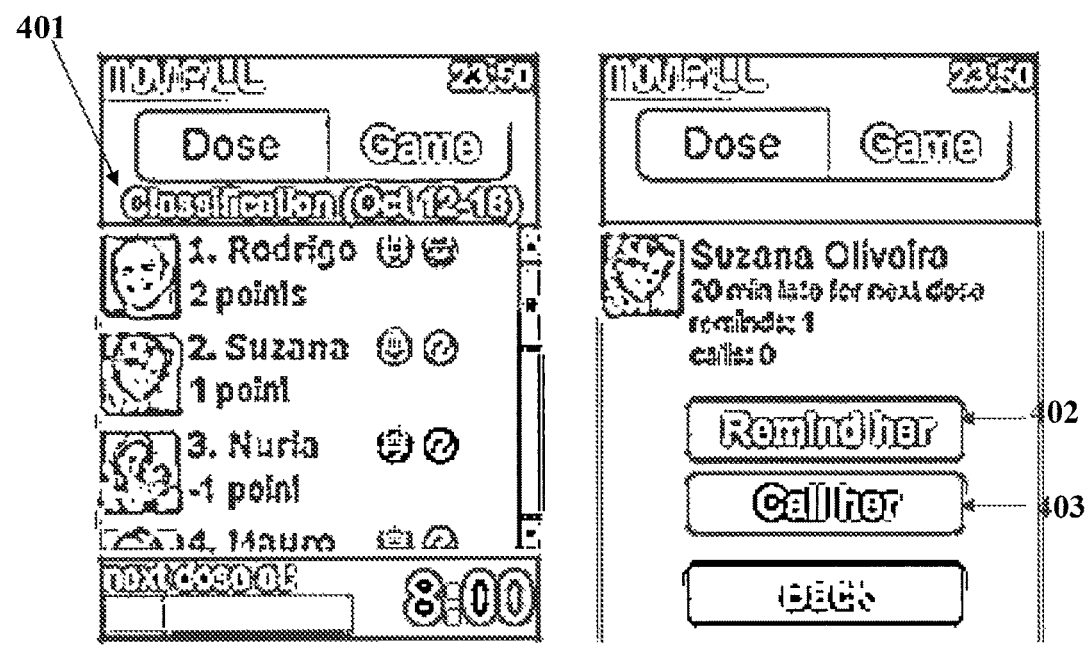
FIG. 4 includes a couple of screenshots showing how social support could be implemented in the present invention.

The invention implements social support using social reminders and live chat. The combination of these strategies with the game can be explained with the following scenario exemplified by the screenshots shown in FIG. 4:

By the end of the day, Rodrigo might be worried that Suzana forgot to take her evening dose. After selecting the player Suzana in the ranking (see Classification list 401 in FIG. 4), Rodrigo can verify that she is actually 20 minutes late to take her next dose and that someone else already sent her a reminder. Now, Rodrigo can decide whether he wants to send her another alert or call her 403 on the phone. After pressing the "Remind her" button 402, he sends an alert to Suzana and, therefore, her mobile phone plays an alarm. If Suzana takes her medication after the alarm was fired, then Rodrigo gets an extra point (the other player that reminded Suzana also gets an extra point). However, Suzana only gets one point because she is more than 15 minutes late.

As explained above, any reminder or phone call to a player that is at least 15 minutes late to take his/her medication is rewarded with an extra point to the patient that sent the reminder. This rule can be seen as a way to distribute the maximum of two points per dose. In the example, if Suzana takes her dose on time (less than ±15 minutes delay), she gets two points and no one else in the game gets extra points by reminding her; but if she is 15 to 30 minutes late, she can only get one point and her lost point goes to her friends that reminded/called her.

The users of the proposed invention can choose from a set of appealing and engaging computer characters (e.g., dog, cat, plant, flower, etc.) and monitor their health according to the character's state (e.g., the dog would look happy if the patient took his/her medicine on time and sick if he/she is late).

Figure 5:
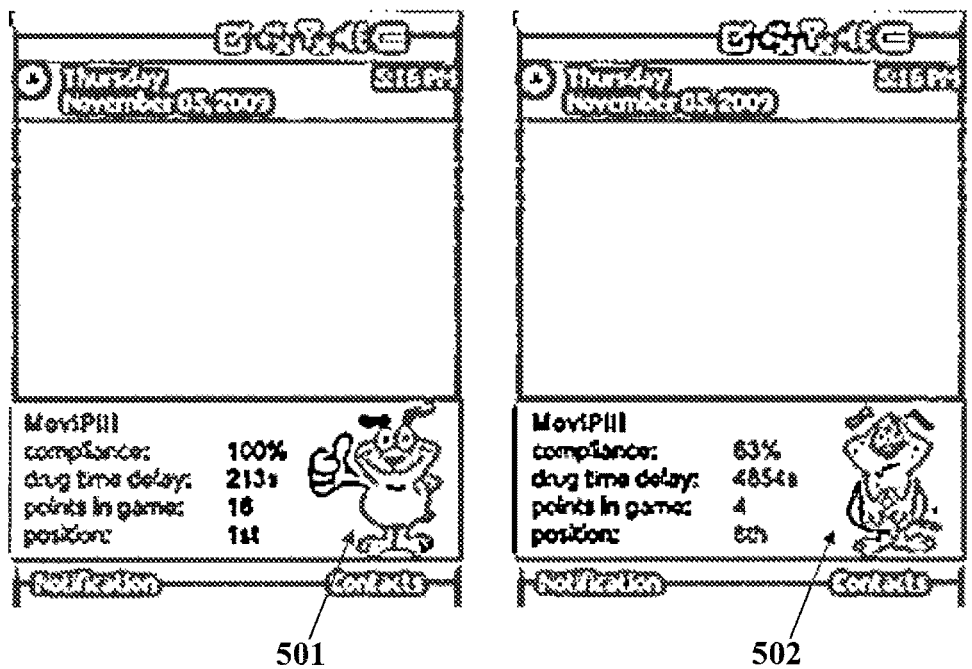
FIG. 5 includes a couple of screenshots showing how personal awareness could be implemented in the present invention.

FIG. 5 shows an implementation example of the personal awareness component (interface) in a smartphone: the system presents the personal status as an active wallpaper. On the left side of FIG. 5, a screen example shown to a patient that is taking his/her medication according to the doctor's prescription (healthy dog 501); on the right side, a screen example presented to a non-compliant patient (sick dog 502).

Figure 6:
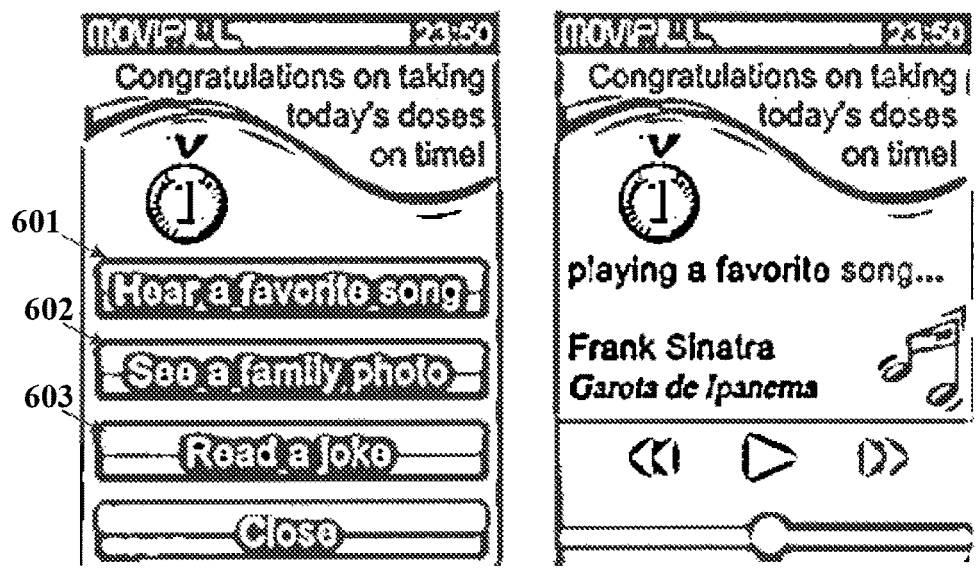
FIG. 6 shows an implementation example of the virtual reward component.

According to the proposed invention, every time the users take their daily medicines at the prescribed time, they receive a symbolic reward. As shown on the left hand side of FIG. 6 the present embodiment includes three rewards that might be appropriate for elders, according to qualitative research recently conducted in situ: hearing a favorite song 601, seeing a photo of their family members 602, and reading a joke/poem 603. The right-hand side of FIG. 6 shows the interface displayed after the user chooses the option "Hear a favorite song" from the menu.

Previous work in the areas of Ubiquitous and Persuasive Computing reports positive changes in people's behavior in a variety of domains when implementing persuasive techniques like social competition, social support and personal awareness. Particularly for medication compliance, commercial products have only focused on personal awareness, such as the MEMS and GlowCaps pillboxes. In this sense, the solution described herein brings novelty by:

1. Proposing a novel solution in the domain of medication compliance that:

a. Scales better to the entire population because it relies on an architecture that benefits from commodity personal computing devices (e.g. mobile phones) and social networks;

b. Enables a straightforward communication means between unknown people suffering from similar illnesses;

c. Encourages social support between unknown people through game dynamics.

2. Proposing a novel social competition in the domain of medication compliance;

3. Proposing a system that is capable of implementing multiple persuasive techniques never combined before to leverage enhanced medication compliance, i.e., social competition, social support, personal awareness, and symbolic rewards;

The results so far are encouraging. A 6-week user study with 18 elders revealed that using the proposed solution reduced non-compliance (forgetting dose intakes) by 60% and increased regimen adherence (taking doses closer to the prescribed time) by 43%. Moreover, improvements to the latter achieved upwards of 56% when considering data from participants which had at least some interest in games, and thus reveal the importance of applying personalized persuasive technologies according to the user's profile and context. Another interesting finding was that a large negative correlation between age and regimen adherence was not significant anymore when elders played the game, which could be evidence that the proposed system helped alleviate age-related memory issues.

As indicated before, the present invention relates to a method and system for improving the medication compliance of a user. It is to be understood that the above disclosure is an exemplification of the principles of the invention and does not limit the invention to the described embodiments.

The invention claimed is:

1. A system for encouraging a user to comply with his/her medication regimen, comprising:
   a plurality of users making use of a method comprising
   registering a group of parameters related to a medication intake of the user, which parameters include a time parameter and a user identifier;
   sending said group of parameters related to a medication intake of the user to a server;
   computing a time difference between said time parameter received and a time parameter associated to the user identifier previously recorded in the server;
   assigning the user with a pre-established number of points depending on the value of said time difference; and
   providing the user with information regarding his/her points obtained for the medication intake;
   wherein each user is provided with means for accessing to information regarding another user's points.

2. The system according to claim 1, further comprising:
   sending an alert to a first user whenever the time difference computed by the server and associated to a second user is greater than a pre-established second threshold.

3. A system for encouraging a user to comply with his/her medication regimen, comprising:
   a register for registering a group of parameters related to a medication intake of the user, which parameters include a time parameter and a user identifier;
   a transmitter for sending said group of parameters related to a medication intake of the user to a server;
   said server being configured to compute a time difference between said time parameter received and a time parameter associated to the user identifier previously recorded in the server;
   said server also being configured to assign the user with a pre-established number of points depending on the value of said time difference; and
   means for providing the user with information regarding his/her points;
   and further comprising at least two users wherein an alert is sent to a first user whenever the time difference of a second user computed by the server is greater than a pre-established second threshold.

* * * * *